(12) United States Patent
Harmon, Sr.

(10) Patent No.: US 7,862,542 B1
(45) Date of Patent: Jan. 4, 2011

(54) FLACCID TUBULAR MEMBRANE AND INSERTION APPLIANCE FOR SURGICAL INTUBATION AND METHOD

(76) Inventor: James V. Harmon, Sr., 56 Pine St., Mahtomedi, MN (US) 55115

( * ) Notice: Subject to any disclaimer, the term of this patent is extended or adjusted under 35 U.S.C. 154(b) by 348 days.

(21) Appl. No.: 11/853,666

(22) Filed: Sep. 11, 2007

Related U.S. Application Data

(60) Provisional application No. 60/843,484, filed on Sep. 11, 2006.

(51) Int. Cl.
*A61M 29/00* (2006.01)

(52) U.S. Cl. .................. 604/103; 604/96.01; 600/115; 600/121; 600/124

(58) Field of Classification Search .............. 600/104, 600/123–125, 156, 207, 115, 116, 121, 208; 604/95.03, 96.01, 97.01, 99.01, 164.01, 164.03, 604/171, 103.05, 103.14, 161, 104, 103.03; 128/898

See application file for complete search history.

(56) References Cited

U.S. PATENT DOCUMENTS

| | | | |
|---|---|---|---|
| 4,657,020 A | 4/1987 | Lifton | |
| 5,441,485 A * | 8/1995 | Peters | 604/101.01 |
| 5,665,064 A | 9/1997 | Bodicky et al. | |
| 5,702,348 A * | 12/1997 | Harhen | 600/124 |
| 5,716,340 A * | 2/1998 | Schweich et al. | 604/101.05 |
| 5,752,518 A | 5/1998 | McGee et al. | |
| 5,938,586 A * | 8/1999 | Wilk et al. | 600/123 |
| 6,142,936 A * | 11/2000 | Beane et al. | 600/207 |
| 6,210,370 B1 * | 4/2001 | Chi-Sing et al. | 604/104 |
| 6,459,919 B1 | 10/2002 | Lys et al. | |
| 6,464,625 B2 | 10/2002 | Ganz | |
| 6,491,618 B1 | 12/2002 | Ganz | |
| 6,522,913 B2 | 2/2003 | Swanson et al. | |
| 6,599,237 B1 | 7/2003 | Singh | |
| 6,808,519 B2 | 10/2004 | Fanelli et al. | |
| 6,890,346 B2 | 5/2005 | Ganz et al. | |
| 6,911,005 B2 * | 6/2005 | Ouchi et al. | 600/121 |
| 6,994,667 B2 * | 2/2006 | Singh | 600/105 |
| 7,009,634 B2 | 3/2006 | Iddan et al. | |
| 7,097,615 B2 | 8/2006 | Banik et al. | |
| 7,199,545 B2 | 4/2007 | Oleynikov et al. | |
| 7,244,251 B2 | 7/2007 | Shehada et al. | |
| RE39,938 E * | 12/2007 | Brain | 128/207.15 |
| 2001/0044595 A1 | 11/2001 | Reydell | |
| 2004/0249362 A1 * | 12/2004 | Levine et al. | 604/523 |

(Continued)

*Primary Examiner*—John P Leubecker
*Assistant Examiner*—Victoria W Chen
(74) *Attorney, Agent, or Firm*—James V. Harmon; Nikolai & Mersereau, P.A.

(57) ABSTRACT

A thin sheath of flexible, flaccid material is introduced through openings in the body of an animal or human patient to permit surgical tools or fluids to be inserted and removed, or debris removed, during surgeries anywhere in the body to protect the tissue of the body from the instruments used. The sheath is inserted by an obturator which holds the sheath thereon by suction through an aperture in the obturator at its distal end. Once the sheath is inserted, suction is removed to release the sheath. Then a balloon on the distal end of the sheath is expanded to hold the sheath in place in the body while the obturator is removed. The sheath then remains in place with the balloon holding the distal end in the open position to enable fluids to flow through the sheath. After a procedure, the balloon is deflated and the sheath removed.

12 Claims, 3 Drawing Sheets

U.S. PATENT DOCUMENTS

| | | |
|---|---|---|
| 2005/0197595 A1 | 9/2005 | Huang et al. |
| 2005/0197627 A1 | 9/2005 | Huang et al. |
| 2006/0009784 A1 | 1/2006 | Behl et al. |
| 2006/0074436 A1 | 4/2006 | Behl |
| 2006/0111611 A1 * | 5/2006 | Eizenfeld et al. ............ 600/124 |
| 2007/0015961 A1 * | 1/2007 | Yamamoto et al. .......... 600/102 |

* cited by examiner

FLACCID TUBULAR MEMBRANE AND INSERTION APPLIANCE FOR SURGICAL INTUBATION AND METHOD

Applicant claims the benefit of Provisional Application Ser. No. 60/834,484 filed Sep. 11, 2006 having the same title which is incorporated herein by reference.

BACKGROUND OF THE INVENTION

1. Field of the Invention

This invention relates the medical arts and more particularly to a flexible protective sheath for subcutaneous insertion into a body such as for facilitating urological, and gastrological procedures.

2. Description of the Related Art

The invention can be used in a variety of surgical fields such as urology and gastroenterology. The invention will be described by way of example in connection with the field of urology. One of the most common urological procedures, both historically and in current practice, is the placement of a catheter in the urethra for the purpose of draining urine or fluid, to diagnose problems or to maintain anatomic continuity. This procedure is performed by inserting the catheter manually while noting any resistance to forward movement as shown by a failure of the catheter to slide smoothly into the urethra. While most placements proceed without problems, typically about ten percent of urinary catheter placements are difficult, causing a substantial burden on the delivery of effective care through the healthcare system. The most common problem is tetany, a spasm of the external urinary sphincter or stricture of the urethra. Stones, and even clots descending from the bladder, also constitute urethral obstructions. In addition, urethral lumen calibers vary considerably, and particularly with urethritis, BPH, urethritis stricture disease and prostate disorders in males. The cost to the healthcare system, hospitals, clinics and doctors' offices is substantial. In addition, the delay in servicing urological catheter patients in a timely manner constitutes poor medical efficiency, delivery and control. When difficulty is encountered, the resulting frustration among healthcare professionals, especially nurses, physician extenders and physician assistants, creates a very real feeling of ineffectiveness on the part of these healthcare workers, to say nothing of the dissatisfaction on the part of the patients caused by the delay and added discomfort. While the dollar cost to the healthcare system is not the only concern, such elements as added labor and material costs, time delays for patient rectification, excess space and equipment required, catheter kit value, nurse technician and physician costs constitute an expense to the healthcare system of surprising proportions. The best available current data indicates about 150,000 urinary catheter placements are made in the United States per day. Of these, about 15,000 are difficult. From this data it can be calculated that the cost to the healthcare system for additional services by healthcare professionals in the United States is over $700 million dollars per year. Moreover, the additional space and equipment amounts to at least $800 million per year for a total added cost of about $1.5 billion per year.

Accordingly, an important object of the present invention is to virtually eliminate these additional costs, greatly improve patient comfort and satisfaction, as well as shortening the time required for catheter placement while adding only a relatively small cost to the equipment required.

Another more specific object of the invention is to eliminate or drastically reduce problems associated with difficult catheter passage through the urethral or other body opening including the following problems among others: the formation of iatrogenic trauma strictures, urethral bleeding, urethral mucosal lining tears, patient pain or discomfort, scar tissue formation, treatment delay, increased infection potential, and inappropriate use of antibiotic which may enhance a recalcitrant immune strain modification of the offending organism.

A further specific object of the invention is to provide an apparatus and method for safely passing a flexible sheath through the urethra of both male and female human patients with a provision for enabling healthcare workers such as nurses and physician's assistants who are not board certified urologists to negotiate most obstructions in a safe, efficient and timely manner without the need of a cystoscope.

In several kinds of surgical operations, e.g., urological procedures, it is the current practice to insert and remove various instruments through the urethra several times during a single surgical operation. The repeated insertion and removal of instruments often requires a significant amount of force. This can of course traumatize the tissue. It is therefore another object of the present invention to eliminate the need for inserting and removing a series of surgical instruments by passing them through an opening in the body in a manner that can cause discomfort or injure the tissue and in that way reduce the possibility of bleeding, trauma, inflammation; infection, false passage, and long-term complications such as scarring.

In addition, the manipulation of a surgical instrument or other object that is partially or completely inserted into the body can also result in damage to the surrounding tissue. A more specific object of the invention is to minimize the possibility of damaging the tissue through either the manipulation or the repeated insertion and removal of instruments that have to be used in succession to complete a surgical operation: For example, in many urologic procedures a cystoscope is inserted blindly or under direct vision for evaluation and diagnosis. The cystoscope is frequently removed and another instrument then inserted for lavage, cauterization, extraction or surgery. A series of such instruments are usually inserted in a logical sequence. Finally, at the conclusion of the endoscopic or percutaneous procedure, it is frequently necessary to insert a rubber tube or sheath as a percutaneous drain or for drainage of the bladder or as a post-op drain. The insertion and removal of each of these other instruments increases the chances for traumatizing or injuring surrounding tissue or even creating a false passage and losing access. As already noted the inventions have applications in a variety of surgical specialties. Each time a body orifice, e.g. oral cavity, urinary, gastrointestinal tract, or other opening is manipulated, the potential for bacteremia is increased. In short, tissue trauma can result from retrograde or antegrade passage instrumentation or removal of foreign bodies. many endoscopic, percutaneous or laparoscopic instruments have a relatively small diameter working channel which limits the size of biopsy specimens. The small size limits the removal of such specimens or foreign bodies by necessitating multiple insertions and withdrawals. This prolongs the operation and is an additional source of tissue trauma.

Flexible catheters have been previously proposed to guide surgical tools as they are inserted into the body of a patient during the course of a surgical procedure. These tools are inserted and removed during a procedure with the object of the catheter being to protect the body from damage and to guide the surgical tools to the desired position. Catheters, now in common use, however have thick walls, typically about 2 mm or more in thickness, which have limited capacity to expand so that some instruments can be passed through the lumen of the catheter only with great difficulty or not at all.

Percutaneous Systems Inc. has proposed the use of a thin walled tube for urethral intubation in U.S. patent application publication 2005/0197627 published Sep. 8, 2005. However there is no way to hold the sheath in place one inserted. Moreover, the sheath has no balloon or passage for introducing an inflation fluid to a balloon. In addition, the sheath is closed at its distal end so that it can be pushed through the urethra.

A thin walled flexible and flaccid sheath is preferable for insertion into the body and to act as a guide as it takes less room than a standard catheter, is not as stiff as a catheter and is expandable and contractible for facilitating instrument insertion and withdrawal. However the insertion and positioning of a thin sheath has been difficult to accommodate largely because of the thin flexible, flaccid walls.

Accordingly the need exists for a sheath which can be easily installed and remain in place during a procedure and works well in conjunction with tools for placing the sheath in the body.

These and other more detailed and specific objects of the present invention will be better understood by reference to the following figures and detailed description which illustrate by way of example of but a few of the various forms of the invention within the scope of the appended claims.

SUMMARY OF THE INVENTION

A sheath is provided which comprises a thin material typically having a wall thickness comparable to that of a condom or a toy balloon. It is flexible and flaccid but strong such that it resists tearing so as to provide a protective barrier in body openings such as the urethra. The sheath comprises a tube with openings at both ends for the passage of surgical instruments for subcutaneous surgeries or a passage for fluids to be inserted or drained. The sheath has an inflatable balloon at or near the distal end to be inflated after insertion to the desired location to keep the mouth of the sheath open and held in place in the body lumen, e.g. within the bladder. The sheath also has a tube that is most preferably extraneous to or bonded to the surface of the sheath for supplying a fluid under pressure to the balloon to inflate it when desired.

The sheath is inserted into the body by means of an obturator. The obturator has an aperture for applying a suction to the sheath for holding it in place on the obturator while the obturator is used to push the sheath into the body. After the sheath, is in place the suction applied to the obturator is shut off and the balloon on the distal end of the sheath is inflated to hold the sheath in place in the body while the obturator is withdrawn, after which fluid may be introduced or removed therethrough into the body and a series of surgical instruments successively introduced and removed through the sheath which remains in place for protecting the tissue of the patient.

The obturator may contain fiber optic cable enabling the operator to see within the body as the sheath is being inserted. The obturator may alternatively have a camera and transmitter to provide wireless images of the body as the sheath is being inserted.

OBJECTS OF THE INVENTION

It is one object of the invention to provide a thin walled tube for use during intubation procedures.

It is another object of the invention to easily place a sheath in a body opening.

It is also an object of the invention to finds a way to secure a flaccid sheath within a body opening.

It is still another object of the invention to provide a sheath for inserting medical procedure instruments subcutaneously to protect the body form injury.

It is yet another object of the invention to provide a sheath for inserting medical procedure instruments in the body easily.

Other objects, advantages and novel features of the present invention will become apparent from the following description of the preferred embodiments when considered in conjunction with the accompanying drawings.

DESCRIPTION OF THE PREFERRED EMBODIMENTS

A sheath 10 in accordance with the present invention is a flexible flaccid and membranous tube with an annular balloon 20 at one end. The sheath functions to protect tissue in a body orifice during subcutaneous surgical procedures or intubations. A very thin sheath is preferred to be more easily inserted and to accept a wider range of surgical tool diameters by being able to expand and contract to the instrument size of the tools being used by the surgeon during the procedures and to be more easily removed after a procedure since it is of a smaller cross section when it has thinner membranous walls.

Figure 1:
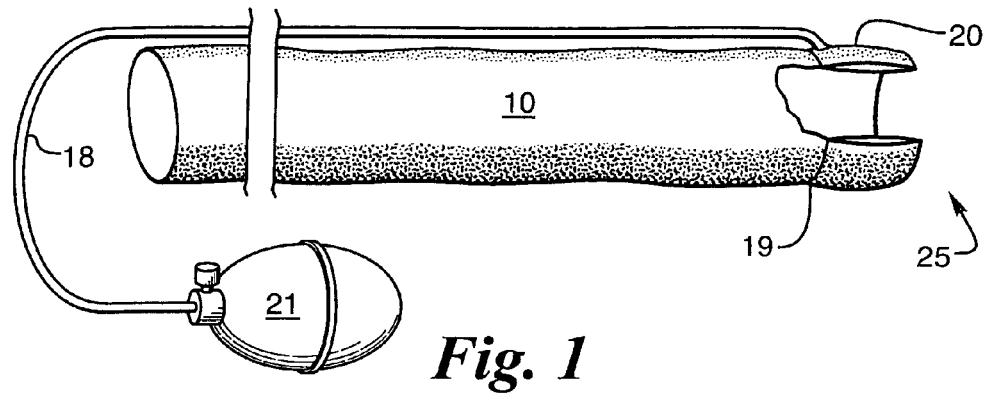
FIG. 1 is a perspective side view of the sheath with a balloon at the distal end.
Figure 1A:
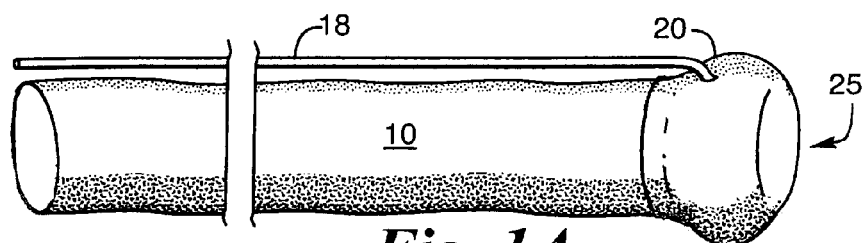
FIG. 1A shows a balloon formed on the end of the sheath.

As shown in FIG. 1 and FIG. 1A a sheath 10 has a balloon 20 formed at the distal end 25 of the sheath. The balloon may be formed by simply manually expanding the free distal end then everting and sliding the sheath material back toward the opposite end and adhesively bonding or otherwise attaching the free edge of the sheath to the underlying material of the sheath at 19 near the distal end. A small tubule 18 typically about 2-3 mm in diameter, which can be either on the inside or the outside of the sheath 10, is used to inflate the balloon. The free end of tubule 18 is connected to a bulb or other source of inflation gas or liquid, and the distal end of the tubule 18 is bonded beneath the free end of the sheath at 19 in communication with the balloon 20. When inflated, the balloon besides holding the sheath in place also acts as a stiffening ring by holding the distal end 25 or mouth of the sheath open after insertion into a body passage. Although the sheath 10 is limp i.e. flaccid, the stiffening ring of inflated material at 20 is surprisingly effective in keeping the distal end open, which is essential to ensure the passage of liquids or instruments etc. through the sheath. Any fluid may be used to inflate the balloon such as air or a saline solution. When it is time to remove the sheath 10 the pressure in the balloon 20 is released.

The sheaths 10 are preferably thin-walled polymeric tubes made from a lubricious polymer or a polymer which may be lubricated on at least one side. The polymeric tube typically has a length from 10 cm to 50 cm and a wall thickness in the range from 0.01 mm to 0.3 mm. An outside diameter of the sheath could be on the order of 1 to 2 cm. The sheath can be made of rubber, plastic or other suitable material such as polymers including polytetrafluoroethylene (PTFE), polyethylene (PE), perfluoroalkoxy (PFA), polyurethane (PU), perfluoromethylvinylether (MFA), perfluoropropylvinylether (PPVE), and the like. One preferred polymer comprises a tensilized PTFE/PPVE copolymer. A preferred elastic polymer comprises natural or synthetic rubber.

While the sheath 10 can be elastic, the tubule 18 is preferably formed from a flexible but inelastic polymer such as PTFE, polyethylene or rubber having a relatively thick wall that will not stretch as pressure is applied. The tubule 18 can be bonded by adhesive in a few places to the surface of the sheath.

Figure 2:
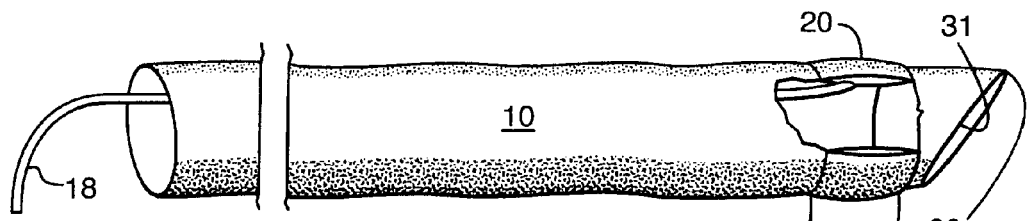
FIG. 2 is a perspective side view of the sheath with a balloon near the distal end.

In a second embodiment as shown in FIG. 2 the sheath 10 has a balloon 20 which is proximate the distal end and is composed of a ring of the same polymeric material or of an elastic material or synthetic rubber adhesively bonded or otherwise secured to the sheath 10 at diameters 22 and 24. A tubule 18 supplies a fluid for pressurizing and expanding the balloon. The distal end of the sheath is cut obliquely at 31 FIG. 6A) to provide an apex for forming a tip 30 that can be wrapped part way or completely around the obturator 12 to compress it against the surface of the obturator for facilitating insertion.

Figure 3:
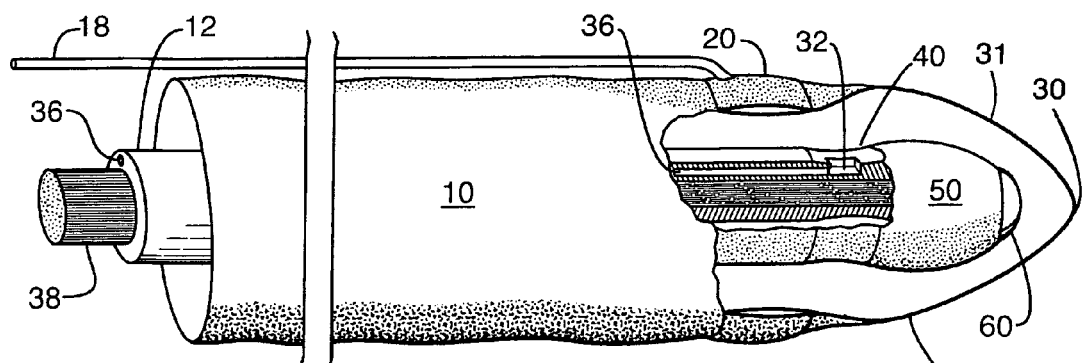
FIG. 3 is a side perspective of a sheath with an obturator having a sheath storage area, and optical fibers with a lens at the tip.

The obturators 12, which can be formed from a stiff or ridged material such as metal or polyethylene which will not buckle during insertion, can come in many different styles for holding and inserting the sheaths 10. In FIG. 3 an obturator 12 has an enlarged head 50 with a tapered nose for inserting the obturator in a body lumen. In the embodiment shown the obturator has a fiber optic cable 38 for enabling the medical personnel to view the urethra, digestive tract, vessel or other body passage as the obturator is being inserted. A lens 60 at the distal end of the tip of the obturator allows the operator to see the inside of the patient. In the embodiment of FIG. 3 a reduced diameter at 40 behind the enlarged head 50 enables the distal end of the sheath 10 which is wrapped around the obturator to be shielded during insertion behind the greater diameter of the enlarged head 50. The apex that provides a point of sheath material 30 is engaged held securely in place on the obturator by being sucked into the end of a passage 36 formed in the wall of the obturator 12 by virtue of the applied a vacuum applied through passage 36 which engages the material 30 at the tip of the sheath and holds the material within the aperture 32 in the wall of the obturator 12 at the end of passage 36. The sheaths can be stored on the obturator in this condition as long as the vacuum is applied and later unfurled when the obturator has been inserted in the patient. Once the sheath is in place the tubule 18 supplies a fluid under pressure for inflating the balloon 20.

Figure 4:
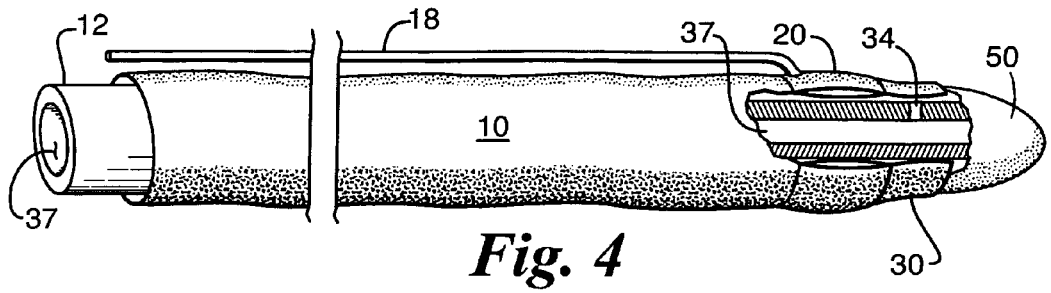
FIG. 4 is a second embodiment of a sheath and an obturator with an open central lumen.

There can be a variety of styles of obturator 12. FIG. 4 shows an embodiment without a reduced diameter at 40 and an aperture 34 from the a center lumen 37 through obturator 12 to engage the sheath material at the tip 30 by a vacuum supplied though the lumen 37 in the center of the obturator 12.

Figure 5:
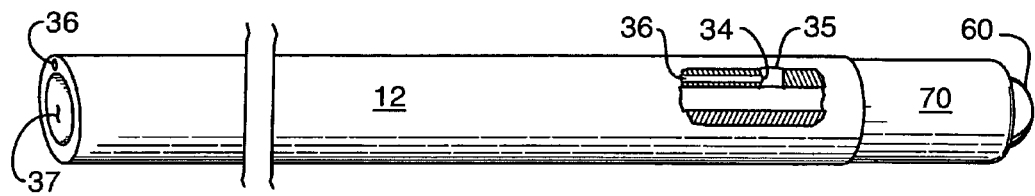
FIG. 5 is a side perspective of an obturator with an aperture for engaging the sheath. and a camera in the tip.

FIG. 5 shows an aperture 34 for providing a vacuum to secure the sheath to the side of the obturator and an aperture 35 connected to a central lumen 37 for inserting medication or lubrication or for evacuation fluids from the body such as blood, urine or other fluids. The embodiment of FIG. 5 shows a miniature electronic wireless television camera 70 at the distal end of the obturator 12. The camera 70 can send signals to the medical personnel wirelessly via a receiver (not shown) to aid in the insertion of the obturator 12 or to provide medical information.

Figure 6:
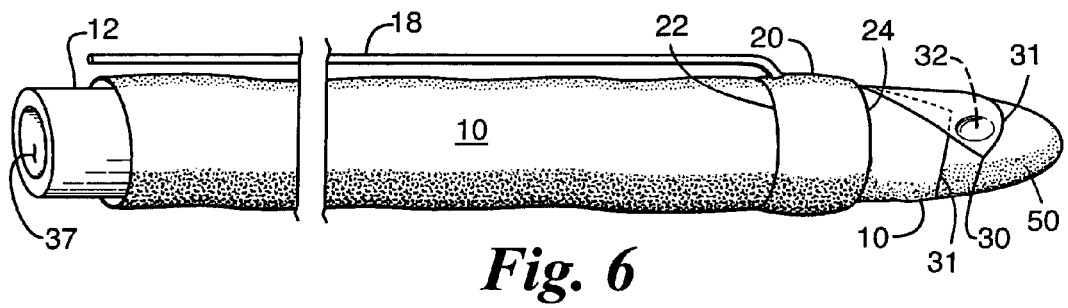
FIG. 6 is a side perspective of an obturator with the oblique end of the sheath wrapped around the distal end of the obturator.
Figure 6A:
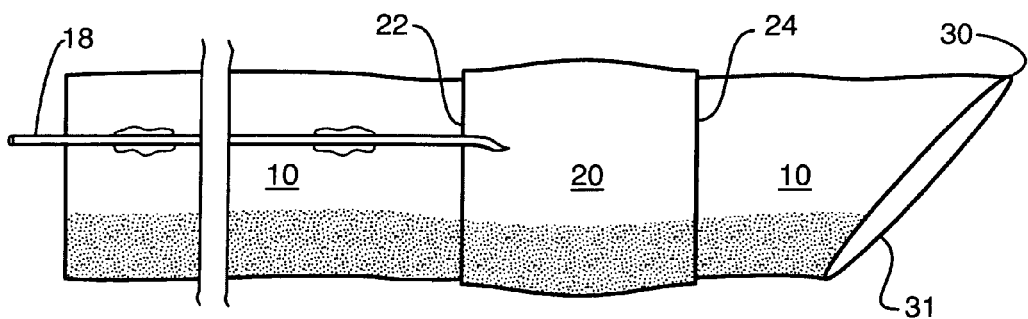
FIG. 6A is a side perspective view of the sheath with oblique end.
Figure 6B:
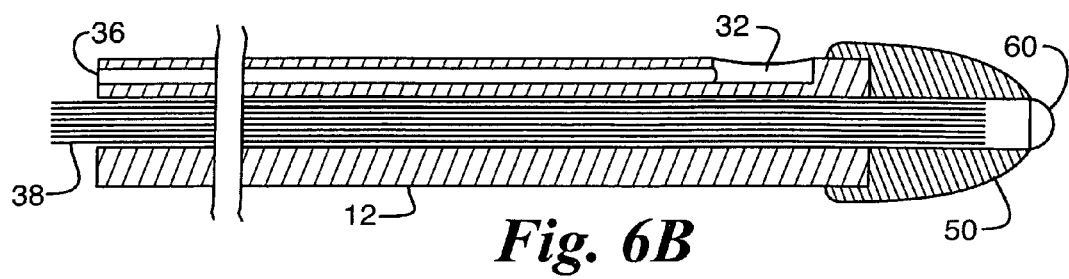
FIG. 6B is a cross section view of the obturator.
Figure 6C:
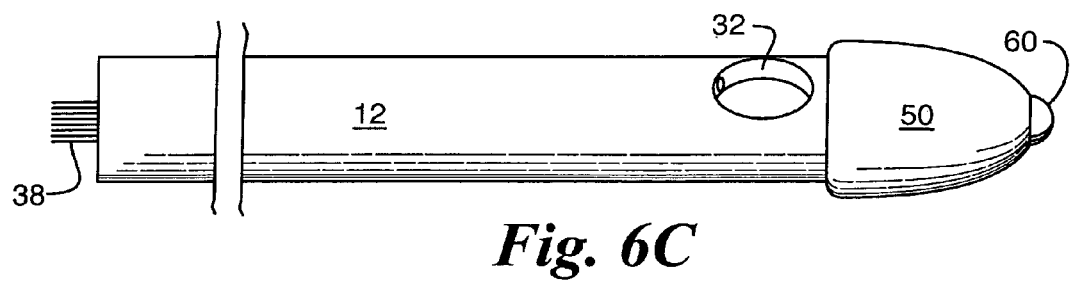
FIG. 6C is a side view of the obturator of FIG. 6B.

FIG. 6 shows another embodiment of an obturator 12 with a sheath 10 having its tip 30 wrapped part way or completely around the obturator at the distal end thereof and secured by suction at aperture 32 thereby enabling it to be drawn in place more reliably through a body passage e.g. the urethra, gastrointestinal tract, or blood vessel. The sheath 10 of FIG. 6 is cut obliquely at the distal end 31 to provide an apex that forms the tip 30 which is wrapped around the obturator and overlays the aperture 32 thereby holding the distal end of the sheath in a compressed coil.

The apertures for providing suction to hold the sheath 10 in place may be at the sides or at the tip of the obturator 12 as the designs of the sheath and obturators vary. The aim is to secure the sheath to the obturator as well as to draw together or compact its distal end during insertion and then to release it while holding the sheath open at the distal end by inflating a balloon or otherwise having a sheath-expanding ring structures activated after the sheath is inserted and is thereafter capable of enabling the ring to be reduced in diameter for removal of the sheath from the body.

U.S. Pat. No. 6,599,237 filed Jan. 10, 2000, issued Jul. 29, 2003 and U.S. Pat. No. 6,994,667 filed Jun. 3, 2003 and issued Feb. 7, 2006 are attached hereto and incorporated herein by reference to show methods for inserting obturators into the body. All references incorporated by reference shall be considered to be disclosed herein as fully and completely as if reproduced in their entirety herein.

It was discovered that the sheath makes it possible to insert and remove a succession of medical instruments, remove material, drain fluids or perform an intubation through the urethra or other body passage even with a very thin membranous sheath that is open at both ends. It also was discovered that by forming the sheath and inflation tubule 18 of different materials or each with a different elasticity, even a membranous sheath can be inflated. It was also found that the stiff ring structure of the balloon 20 is effective in spreading the mouth of the sheath inside the body thereby holding it open. Wrapping the tip 30 around the obturator and placing it behind the head 50 was found to enhance reliable insertion of the sheath through a tight passage.

Obviously, many modifications and variations of the present invention are possible in light of the above teachings. It is therefore to be understood that, within the scope of the appended claims, the invention may be practiced otherwise than as specifically described.

What is claimed is:

1. A method for insertion of a surgical intubation sheath into a body of an animal or human patient comprising:
   providing a tubular obturator,
   providing a flaccid membranous tubular sheath comprising flexible polymeric material with a central lumen that is open at its proximal end and has a distal open mouth comprising an end portion of the sheath wherein the mouth is formed from flaccid sheath material surrounding the obturator that is unattached thereto,
   applying a vacuum to an aperture in the side of the obturator,
   placing a portion of the flexible sheath over the aperture on the obturator to enable the vacuum to apply a suction force for holding the sheath to the obturator, thereafter inserting the obturator into a body cavity of a patient with the sheath held thereto by the applied vacuum, providing an annular inflation balloon at the mouth of the sheath, inflating the balloon at the distal end of the sheath for opening the distal mouth of the sheath within the body of the patient to thereby form a stiffening ring structure in the flaccid sheath proximate the distal mouth to spread, stiffen and hold open the mouth inside the patient's body when the sheath is in the desired location, such that the spreading and stiffening of the flaccid mouth facilitates the passage of fluids or surgical instruments therethrough into or out of the body of the patient, removing the vacuum such that the suction force holding the sheath to the obturator is released, and withdrawing the obturator from the body while the sheath remains held in place therein by the inflated ring structure that serves to spread and hold open the distal mouth thereof.

2. A method for insertion of a surgical intubation sheath into a body of an animal or human patient as in claim 1 including, providing the obturator with fiber optics and observing progress of the obturator through the body cavity by fiber optics to aid in the insertion process.

3. A method for insertion of a surgical intubation sheath into a body of an animal or human patient as in claim 1 including, observing the obturator progress through the body cavity by use of a television camera and associated transmitter, receiver and viewer to aid in the insertion process.

4. A method for insertion of a surgical intubation sheath into or out of the body of the patient into a body of an animal or human patient as in claim 1 including, deflating the balloon and removing the sheath from the body.

5. A method for insertion of a surgical intubation sheath into a body of an animal or human patient as in claim 1 including, inserting and withdrawing one or more surgical tools though the sheath during a surgical procedure.

6. A method for insertion of a surgical intubation sheath into a body of an animal or human patient as in claim 5 including, deflating the balloon and removing the sheath from the body.

7. The method of claim 1 including the steps of, attaching as an entity separate from the sheath a flexible but relatively inelastic extraneous inflation tubule in fluid communication with the balloon, extending the tubule along the length of the sheath to place a proximal end of the tubule outside of the body of the patient and introducing a liquid or gas into the proximal end of the tubule for inflating the balloon.

8. The method of claim 7 including the step of, forming the balloon from an elastic polymer to enable the balloon to stretch outwardly when inflated for forming the stiffening ring structure at the distal end of the sheath to spread and hold open the distal end of the sheath within the patient.

9. The method of claim 1 including the steps of, providing the obturator with an enlarged head, and placing a distal end of the sheath behind the greater diameter of the enlarged head to thereby enhance insertion of the sheath through a tight passage.

10. The method of claim 1 including the step of partially or completely wrapping the distal end of the sheath around the obturator adjacent the location of the aperture provided in the obturator to thereby facilitate attachment of the sheath to the obturator.

11. The method of claim 1 including the step of forming the balloon by everting a free distal end of the sheath, sliding the everted end back toward the proximal end of the sheath and bonding the free everted end of the sheath to adjacent sheath material.

12. The method of claim 1 including the step of providing a flexible inflation tubule extraneous to the sheath and bonding an end thereof in communication with the balloon for inflating the balloon through the extraneous tubule.

* * * * *